United States Patent [19]

Murakami et al.

[11] 4,145,363

[45] Mar. 20, 1979

[54] 4-CARBAMOYLAMINO-α-AMINOMETHYL-BENZYL ALCOHOL DERIVATIVES

[75] Inventors: Masuo Murakami; Kozo Takahashi, both of Tokyo; Kiyoshi Murase, Urawa; Toshiyasu Mase, Tokyo; Hisashi Ida, Urawa; Toichi Takenaka, Tokyo, all of Japan

[73] Assignee: Yamanouchi Pharmaceutical Co., Ltd., Tokyo, Japan

[21] Appl. No.: 809,998

[22] Filed: Jun. 27, 1977

Related U.S. Application Data

[62] Division of Ser. No. 651,738, Jan. 23, 1976, Pat. No. 4,063,025.

[30] Foreign Application Priority Data

| | | |
|---|---|---|
| Feb. 5, 1975 [JP] | Japan | 50-14993 |
| May 24, 1975 [JP] | Japan | 50-62207 |
| Dec. 26, 1975 [JP] | Japan | 50-157348 |

[51] Int. Cl.$^2$ .................. C07C 127/17; A61K 31/17
[52] U.S. Cl. .................... 260/553 A; 260/553 C; 424/322
[58] Field of Search ................. 260/553 A, 553 C

[56] References Cited

U.S. PATENT DOCUMENTS

| | | | |
|---|---|---|---|
| 3,644,520 | 2/1972 | Hartley et al. | 260/553 A X |
| 3,689,524 | 9/1972 | Jack et al. | 260/553 A X |
| 3,930,016 | 12/1975 | Berntsson et al. | 260/553 A X |
| 3,935,259 | 1/1976 | Wilhelm | 260/553 A |
| 3,944,611 | 3/1976 | Smith | 260/553 A X |
| 3,959,369 | 5/1976 | Smith | 260/553 A X |
| 3,998,790 | 12/1976 | Brändström et al. | 260/553 A X |
| 4,015,011 | 3/1977 | Schromm et al. | 260/553 A X |
| 4,041,075 | 8/1977 | Smith | 260/553 A X |

FOREIGN PATENT DOCUMENTS

| | | |
|---|---|---|
| 2181828 | 12/1973 | France. |
| 1260893 | 1/1972 | United Kingdom ................. 260/553 A |
| 1383899 | 2/1975 | United Kingdom ................. 260/553 A |
| 1393675 | 5/1975 | United Kingdom ................. 260/553 A |
| 1396322 | 6/1975 | United Kingdom ................. 260/553 A |

*Primary Examiner*—Thomas Waltz
*Attorney, Agent, or Firm*—Burgess, Ryan and Wayne

[57] ABSTRACT

There are disclosed novel 4-substituted amino-α-aminomethylbenzyl alcohol derivatives represented by the formula:

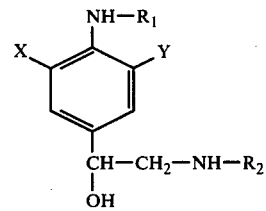

wherein X represents a halogen atom; Y represents a hydrogen atom or a halogen atom; $R_1$ represents a lower alkyl group, a carbamoyl group, a mono- or di-lower alkyl-substituted carbamoyl group, a phenyl-substituted carbamoyl group, a lower alkoxycarbonyl group, a lower alkoxy-substituted lower alkoxycarbonyl group, a phenyl-substituted lower alkoxycarbonyl group, or a cycloalkyloxycarbonyl group; and $R_2$ represents a lower alkyl group, a cycloalkyl group, or the group shown by the

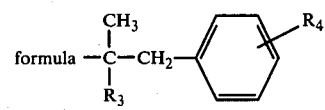

wherein $R_3$ represents a hydrogen atom or a lower alkyl group and $R_4$ represents a hydrogen atom, a hydroxy group, or a lower alkoxy group and the pharmaceutically acceptable nontoxic salts thereof.

These compounds are antiasthmatic agents useful for the prophylaxis and treatment of asthma.

3 Claims, No Drawings

4-CARBAMOYLAMINO-α-AMINOMETHYLBENZYL ALCOHOL DERIVATIVES

This is a division of application Ser. No. 651,738, filed Jan. 23, 1976, now U.S. Pat. No. 4,063,025.

BACKGROUND OF THE INVENTION

1. Field of the Invention

The present invention relates to novel benzyl alcohol derivatives and more particularly to novel 4-substituted amino-α-aminomethylbenzyl alcohol derivatives and the pharmaceutially accepable nontoxic salts thereof.

2. Description of the Prior Art

Various compounds having bronchodilator activity are known and among them Isoproterenol and Salbutamol are well known as a bronchodilating agent and are commercially available. In the prophylactic treatment of asthma, it is desirable that a medicament showing bronchodilator activity be administered orally. However, although commercially available medicaments show strong bronchodilator activity by parenteral adminstration such as by intravenous injection, or by aerosol adminstration, etc., the bronchodilator activity of these medicaments is not sufficiently strong when they are orally administered. Thus, there has been an urgent need for the discovery of a medicament showing a strong bronchodilator activity by oral adminstration.

Now, recently, it was reported that 1-(4-amino-3,5-dichlorophenyl)-2-tert-butylamino ethanol (referred to as NAB 365) shown by the formula:

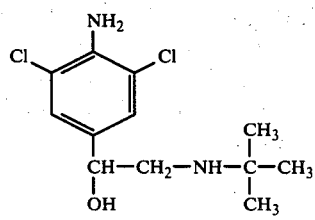

showed a strong bronchodilator activity by oral administration (see, Arzneim, Forsch; 22(5), 861–876(1972)). The report discloses that the bronchodilator activity of NAB 365 by oral administration is about 500 times stronger than that of Isoproterenol and about 100 times stronger than that of Salbutamol.

SUMMARY OF THE INVENTION

As a result of various investigations under such a technical level, the inventors have discovered that among the compounds obtained by introducing various substituents to the amino group at the 4-position of NAB 365 the compounds of this invention show a stronger bronchodilator activity than that of NAB 365 by oral administration and further the activity is selective.

According to the present invention, there are provided novel 4-substituted amino-α-aminomethylbenzyl alcohol derivatives shown by formula:

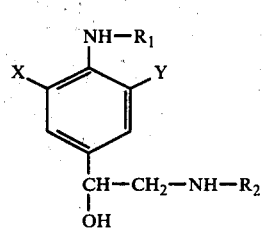

wherein X represents a halogen atom; Y represents a hydrogen atom or a halogen atom; $R_1$ represents a lower alkyl group, a carbamoyl group, a mono- or di-lower alkyl-substituted carbamoyl group, a phenyl-substituted carbamoyl group, a lower alkoxycarbonyl group, a lower alkoxy-substituted lower alkoxycarbonyl group, a phenyl-substituted lower alkoxycarbonyl group, or a cycloalkyloxycarbonyl group; and $R_2$ represents a lower alkyl group, a cycloalkyl group, or the group shown by the

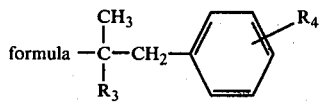

wherein $R_3$ represents a hydrogen atom or a lower alkyl group and $R_4$ represents a hydrogen atom, a hydroxy group, or a lower alkoxy group and the pharmaceutially acceptable nontoxic salts of them.

The compounds of this invention are useful as medicaments which show a relatively high activity more effectively to the smooth muscles of respiratory organs than to the cardiac muscles and show directly a bronchodilator activity by stimulation of a β-adrenergic receptor. In particular, the compounds of this invention have a selective bronchodilator activity by oral administration and thus they can be used as an excellent anti-asthmatic agent for the prophylaxis and treatment of an asthma.

DESCRIPTION OF THE PREFERRED EMBODIMENTS

As described above, the compounds of this invention are shown by formula I. As suitable examples of the halogen atoms shown by X and Y in the formula, there are illustrated a chlorine atom and a bromine atom. Also, suitable examples of $R_1$ in said formula are a lower alkyl group such as methyl group, ethyl group, propyl group, isopropyl group, butyl group, tert-butyl group, amyl group, etc.; a carbamoyl group; a mono- or di-lower alkylcarbamoyl group such as methylcarbamoyl group, dimethylcarbamoyl group, ethylcarbamoyl group, propylcarbamoyl group, isopropylcarbamoyl group, tert-butylcarbamoyl group, diethylcarbamoyl group, ethylmethylcarbamoyl group, etc.; a lower alkoxycarbonyl group such as methoxycarbonyl group, ethoxycarbonyl group, propoxycarbonyl group, isopropoxycarbonyl group, butoxycarbonyl group, tert-butoxycarbonyl group, amyloxycarbonyl group, etc.; a lower alkoxy-substituted lower alkoxycarbonyl group such as ethoxymethoxycarbonyl group, (2-ethoxy)ethoxycarbonyl group, (2-methoxy)ethoxycarbonyl group, etc.; a phenyl-substituted alkoxycarbonyl group such as benzyloxycarbonyl group, phenethyloxycarbonyl group, α-methylphenethyloxycarbonyl group, etc.; and a cycloalkyloxycarbonyl group such as cyclohexyloxycarbonyl group, cyclopentyloxycarbonyl group, cyclopropyloxycarbonyl group, etc. Examples of $R_2$ are a lower alkyl group such as methyl group, ethyl group, propyl group, isopropyl group, butyl group, isobutyl group, sec-butyl group, tert-butyl group, tert-amyl group, etc.; a cycloalkyl group such as cyclopropyl group, cyclobutyl group, cyclopentyl group, cyclohexyl group, etc.; and examples of $R_3$ shown by the formula

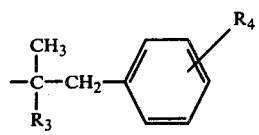

are a hydrogen atom; and a lower alkyl group such as methyl group, ethyl group, isopropyl group, butyl group, etc., and further examples of $R_4$ are a hydrogen atom; a hydroxy group; and a lower alkoxy group such as methoxy group, ethoxy group, isopropyloxy group, butoxy group, etc.

The preferred homologs of the compounds of this invention are the compounds of formula I in which $R_2$ is a tert-butyl group. The more preferable homologs of the compounds of this invention are the compounds of in the formula 1 in which $R_1$ is a lower alkoxycarbonyl group and $R_2$ is a tert-butyl group. Also, the most preferred compounds of this invention are the compounds of the formula 1 in which $R_1$ in the formula is an ethoxycarbonyl group, $R_2$ is a tert-butyl group, and X and Y each is a chlorine atom. That is, the practical examples of the most preferred compound of this invention are 3,5-dichloro-4-ethoxycarbonylamino-α-(tert-butylaminomethyl)benzyl alcohol and the pharmaceutially acceptable nontoxic salts thereof.

Furthermore, as the pharmaceutially acceptable nontoxic salts of the compounds of this invention, there are the acid addition salts thereof with a mineral acid such as hydrochloric acid, hydrobromic acid, phosphoric acid, etc., or an organic acid such as maleic acid, fumaric acid, acetic acid, etc.

Now, the compound of this invention shown by formula I can be prepared by reacting the compound shown by formula: II

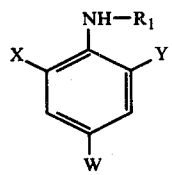                                II wherein X, Y, and $R_1$ have the same meaning as in formula I and W represents

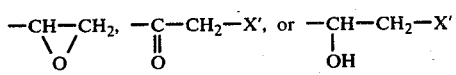

(wherein X' represents a halogen atom) and the amine shown by formula III

                                III wherein $R_2$ and $R_3$ have the same meaning as in formula I and, if desired, reducing the reaction product thus obtained.

In more detail, at the practice of the aforesaid reaction, the compound of formula II is reacted with an equimolar or excessive amount of the amine of formula III in an organic solvent such as chloroform, isopropyl alcohol, ethanol, acetonitrile, ethyl acetate, dimethyl formamide, etc. In this case, it is preferred for carrying out the reaction smoothly, to add an acid binding agent such as sodium carbonate, potassium carbonate, etc., to the reaction mixture. The reaction usually proceeds sufficiently when carried out for from 30 minutes to 3 hours at room temperature or under heating but the reaction conditions may be properly selected in wide ranges according to the nature of the starting materials. That is, there is no particular limitation about the reaction temperature and reaction period of time but the temperature is preferably from $-30°$ C. to $100°$ C. and the reaction period of time is preferably from 30 minutes to 48 hours.

When in the aforementioned reaction the compound of formula II wherein W is the group shown by

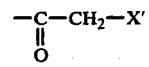

is used as the starting material, the reaction product thus obtained is then reduced. The reduction can be easily carried out by treating the reaction product with a reducing agent such as sodium borohydride, lithium aluminum hydride, etc., in an organic solvent such as methanol, ethanol, ethyl acetate, chloroform, ether, tetrahydrofuran, etc., usually at room temperature or, if desired, under ice-cooling.

Further, when the compound of formula II wherein W is the group shown by

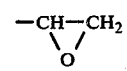

is used as the starting material the reaction, it is preferred to heat the compound and the amine of formula III in a sealed tube.

In addition, when the compound of formula II wherein $R_1$ is a carbamoyl group is used, the reaction is sometimes accompanied by an amine exchange reaction at the same time to form a compound wherein the amino group in the carbamoyl group has been converted into the amine of formula III. This reaction is shown as follows.

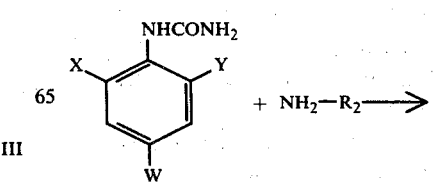

-continued (1949)) using 4-8 groups and one group consists of 4-8 guinea pig.

The results are shown in the following Table I.

Table I

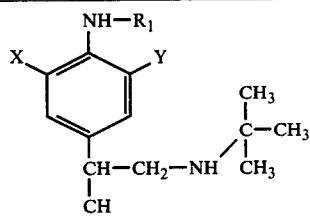

| Sample | $R_1$ | X | Y | | anti-asthmatic activity $ED_{50}(\mu g/Kg)$ |
|---|---|---|---|---|---|
| Known compound NAB 365 | H | Cl | Cl | hydrochloride | 490 |
| Present compound | | | | | |
| Ex. 6 | —$C_2H_5$ | Cl | Cl | hydrochloride | 125–250 |
| Ex. 8 | —COOCH$_3$ | Br | Br | ½ fumarate | 125 |
| Ex. 12 | —COOCH(CH$_3$)$_2$ | Cl | Cl | hydrochloride | 32 |
| Ex. 13 | —COOCH$_2$—C$_6$H$_5$ | Cl | Cl | hydrochloride | 125 |
| Ex. 14 | —COOCH$_2$CH$_2$OCH$_3$ | Cl | Cl | hydrochloride | 32 |
| Ex. 15 | —CONHCH$_3$ | Cl | Cl | free base | 125–250 |
| Ex. 18 | —COOCH$_3$ | Br | Cl | ½ fumarate | 63 |
| Ex. 23 | —COOCH$_3$ | Cl | H | ½ fumarate | 63–125 |

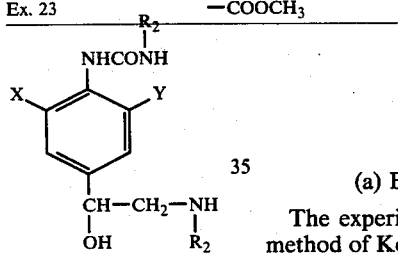

The compound of formula I thus prepared may be isolated and purified by known chemical operations such as concentration, recrystallization, column chromatography, etc.

The compound of this invention can be administered orally as, for example, tablets, capsules, etc., or parenterally as, for example an intravenous injection, aerosol, etc. Also, when the compound of this invention is orally administered to an adult, the proper dosage thereof is 10–50 μg./day.

The experimental results obtained by testing the bronchodilator activity of the compounds of this invention are shown below together with the comparison results made with NAB 365:

EXPERIMENT I (Anti asthmatic activity)

The experiments were carried out according to the method of Parker et al., (J. Pharmacol. Exptl. Therap., 118, 359–364 (1956)). A guinea pig was placed in a 11 liters glass chamber and exposed to the spasmogen by means of a nebulizer. When 0.1% histamine dihydrochloride was sprayed into the chamber, the guinea pig showed a symptom of dyspnea. Samples were administered subcutaneously to animals 30 min. prior the application of the spasmogen. If the guinea big showed no asthmatic dyspnoic symptoms, the sample was evaluated to be effective.

$ED_{50}$ was calculated by the method of Litchfield-Wilcoxon (J. Pharmacol. Exptl. Therap., 96, 99–113

EXPERIMENT II (a) Bronchodilator activity, $\beta_2$ action

The experiments were carried out according to the method of Konzett and Rossler (Arch. exp. Path. Pharmakol., 195, 11–14 (1940)). Mongrel dogs were anesthetized with pentobarbital Na. Temporary increase in bronchial resistance, measured with transducer connected to a polygraph, were produced by histamine dihydrochloride, 10 μg/Kg injected rapidly intravenously at intervals of 30 min. The test samples were injected intraduodenally and the time-course of antihistamine activity of the sample (the inhibition rate (%) against the control) was obtained.

$ED_{50}$ (μg/Kg) values of α-antagonists were obtained from the dose response curve drawn according to the peak effect on each dose. The results are shown in the Table II.

(b) Action on heartrate, $\beta_1$ action

Mongorel dogs were anesthetized with pentobarbital Na. Heart rate (HR) was recorded on polygraph. The samples were administered intra-duodenally and the HR was observed at varying intervals after the administration. The time-course of ΔHR (the increased HR against the control) was obtained.

The dose response curve drawn according to the peak response on each dose and the $ED_{25}$ beats/min. (μg/Kg), that is the dose of the sample producing 25 beats/min. increase in heart rate was obtained from the curve. The results are shown in the following Table II.

(c) Broncho-selectivity

The broncho-selectivity was obtained by the following equation.

$$\text{Broncho-selectivity} = \frac{ED_{25} \text{ beats/min. of } \beta_1 \text{ action}}{ED_{50} \text{ of } \beta_2 \text{ action}}$$

Table II

| Sample | $\beta_2$ action i.d. $ED_{50}$ (μg/Kg) | $\beta_1$ action i.d. $ED_{25}$ beats/min (μg/Kg) | broncho-selectivity (Ratio of $\beta_1/\beta_2$) |
|---|---|---|---|
| 1-(4-amino-3,5-dichloro-phenyl)-2-tert-butylamino ethanol hydrochloride (NAB 365) | 12.3 | 5.7 | 0.46 |
| 3,5-dichloro-4-ethoxycarbonyl-amino-α-(tert-butylaminomethyl)-benzyl alcohol hydrochloride (compound of Ex. 10) | 4.5 | 19.5 | 4.3 |

Reference example 1

After gradually adding a solution of 5.5 g. of bromine in 5 ml. of chloroform to a solution of 7.5 g. of 3,5-dichloro-4-methylaminoacetophenone in 60 ml. of chloroform with stirring at 40°–50° C., the mixture was further stirred under heating until the color of bromine had disappeared. The white crystals formed were collected by filtration, washed with chloroform, and dried to provide 12.5 g. of a crude product. The crude product was suspended in 50 ml. of chloroform and after adding thereto a saturated aqueous sodium bicarbonate solution followed by shaking, the chloroform layer formed was recovered and dried over anhydrous magnesium sulfate. The mixtue was filtered and the filtrate was concentrated under reduced pressure to provide 8.5 g. of 3,5-dichloro-4-methylamino-α-bromoacetophenone having a melting point of 85°–87° C.

Reference example 2

(a) A mixture of 4 g. of 3,5-dichloro-4-aminoacetophenone, 12 ml. of phosgene, and 30 ml. of toluene was heated for 24 hours at 150° C. in a sealed tube. The reaction mixtue was then cooled and concentrated under reduced pressure to povide 4.0 g. of 2,6-dichloro-4-acetylphenyl isocyanate having a melting point of 82°–84° C.

(b) In 50 ml. of toluene was dissolved 3.9 g. of 2,6-dichloro-4-acetylphenyl isocyanate and after adding 2 ml. of absolute methanol to the solution, the mixture was stirred overnight at 100° C. The reaction mixture was cooled and then concentrated under reduced pressure and the residue obtained was recrystallized from a mixture of benzene and n-hexane to provide 4.33 g. of 3,5-dichloro-4-methoxycarbonylaminoacetophenone having a melting point of 107°–109° C.

(c) In 30 ml. of chloroform was dissolved 2 g. of 3,5-dichloro-4-methoxycarbonylaminoacetophenone and then a solution of 1.22 g. of bromine in 5 ml. of chloroform was added to the solution with stirring at room temperature. After further stirring the mixture for 30 minutes, the mixture was concentrated under reduced pressure, whereby crystals were formed. The crystals were recrystallized from a mixture of benzene and n-hexane to provide 2.07 g. of 3,5-dichloro-4-methoxycarbonylamino-α-bromoacetophenone having a melting point of 140°–141° C.

Reference example 3

In 14 ml. of absolute methanol was dissolved 0.5 g. of 3,5-dichloro-4-methoxycarbonylamino-α-bromoacetophenone and after cooling the solution to 5° C., 0.05 g. of sodium borohydride was added thereto followed by stirring for one hour. Then, after acidifying the solution by adding thereto 2 ml. of a 1.44 N hydrogen chloride-ethanol solution under cooling, an excessive amount of sodium carbonate was immediately added to the mixture followed by stirring for 10 minutes. The reaction mixture was concentrated under reduced pressure and the residue was dissolved in 30 ml. of chloroform. The solution was washed with a saturated aqueous sodium chloride solution and dried over anhydrous magnesium sulfate. The mixture was filtered and the filtrate was concentrated under reduced pressure to provide 0.4 g. of 3,5-dichloro-4-methoxycarbonylamino-α-bromomethylbenzyl alcohol.

Nuclear magnetic resonance spectra (CDCl$_3$): δ: 2.92 (d, 1H, >CH—OH), 3.50 (m, 2H, —CH$_2$Br), 3.73 (s, 3H, —OCH$_3$), 4.84 (m, 1H, >CH—), 7.36 (S, 2H, H of a benzene ring).

Reference example 4

A solution of 1 g. of bromine in 2 ml. of chloroform was gradually added to a solution of 1.8 g. of 3,5-dibromo-4-methylaminoacetophenone in 20 ml. of chloroform with stirring at 40°–50° C., whereby crystals were formed. The crystals thus formed were recovered by filtration and after adding water to the crystals, the mixture was extracted with benzene. The benzene extract obtained was washed with water and dried over anhydrous magnesium sulfate. The mixture was filtered and the filtrate formed was concentrated under reduced pressure to provide the crystals of 3,5-dibromo-4-methylamino-α-bromoacetophenone. By washing the crystals with isopropylalcohol and drying, 1.7 g. of 3,5-dibromo-4-methylamino-α-bromoacetophenone having a melting point of 87°–89° C. was obtained.

Reference example 5

By following the similar procedure as in Reference example 4 using a solution of 30 ml. of chloroform containing 3.5 g. of 3,5-dichloro-4-ethylaminoacetophenone prepared by dichlorinating p-ethylaminoacetophenone and a solution of 2.5 g. of bromine in 3 ml. of chloroform, 2.7 g. of 3,5-dichloro-4-ethylamino-α-bromoacetophenone having a melting point of 58°–59° C. was obtained.

Reference example 6

By following the similar procedure as in Reference example 2-a) using 2 g. of 4-amino-3,5-dibromoacetophenone and 2 g. of phosgene, 2,6-dibromo-4-acetylphenyl isocyanate was obtained and then by treating the product with the similar procedure as in Reference example 2-b), 1.7 g. of 3,5-dibromo-4-methoxycarbonylaminoacetophenone having a melting point of 141°–142° C. was obtained.

Furthermore, by following the similar procedure as in Reference example 4 using 1.3 g. of 3,5-dibromo-4-methoxycarbonylaminoacetophenone and 0.6 g. of bromine, 1.4 g. of 3,5-dibromo-4-methoxycarbonylamino-α-bromoacetophenone having a melting point of 156°–158° C. was obtained.

Reference example 7

In 50 ml. of toluene was dissolved 5 g. of 2,6-dichloro-4-acetylphenyl isocyanate and after adding 5 ml. of absolute ethanol, the mixture was treated with the similar procedure as in Reference example 2-b) to provide 5.2 g. of 3,5-dichloro-4-ethoxycarbonylaminoacetophenone having a melting point of 105°–107° C.

Furthermore, by following the similar procedure as in Reference example 2-c) using 6.18 g. of 3,5-dichloro-4-ethoxycarbonylaminoacetophenone and 3.58 g. of bromine, 6.23 g. of 3,5-dichloro-4-ethoxycarbonylamino-α-bromoacetophenone having a melting point of 144°–146° C. was obtained.

Reference example 8

By following the similar procedure as in Reference example 2-b) using 5 g. of 2,6-dichloro-4-acetylphenyl isocyanate and 10 ml. of anhydrous n-propyl alcohol, 4.96 g. of 3,5-dichloro-4-n-propoxycarbonylaminoacetophenone having a melting point of 77°–78° C. was obtained.

Furthermore, by following the similar procedure as in Reference example 2-c) using 4.83 g. of 3,5-dichloro-4-n-propoxycarbonylaminoacetophenone and 2.67 g. of bromine, 5.1 g. of 3,5-dichloro-4-n-propoxycarbonylamino-α-bromoacetophenone having a melting point of 103°–106° C. was obtained.

Reference example 9

By following the similar procedure as in Reference example 2-b) using 5 g. of 2,6-dichloro-4-acetylphenyl isocyanate and 10 ml. of anhydrous isopropyl alcohol, 5.92 g. of 3,5-dichloro-4-isopropoxycarbonylaminoacetophenone having a melting point of 95°–97° C. was obtained.

Furthermore, by following the similar procedure as in Reference example 2-c) using 5.92 g. of 3,5-dichloro-4-isopropoxycarbonylaminoacetophenone and 3.27 g. of bromine, 6.5 g. of 3,5-dichloro-4-isopropoxycarbonylamino-α-bromoacetophenone having a melting point of 122°–125° C. was obtained.

Reference example 10

In 70 ml. of toluene was dissolved 5 g. of 2,6-dichloro-4-acetylphenyl isocyanate and after adding 3 g. of anhydrous benzyl alcohol to the solution, the mixture was stirred overnight at 60° C. The reaction mixture was cooled, washed thrice each with 100 ml. of water, and dried over anhydrous magnesium sulfate. The mixture was filtered and the filtrate obtained was concentrated under reduced pressure. By recrystallizing the residue formed from a mixture of benzene and n-hexane, 6.6 g. of 3,5-dichloro-4-benzyloxycarbonylaminoacetophenone having a melting point of 106°–108° C. was obtained.

Furthermore, by following the similar procedure as in Reference example 2-c) using 6.5 g. of 3,5-dichloro-4-benzyloxycarbonylaminoacetophenone and 3.1 g. of bromine, 7.48 g. of 3,5-dichloro-4-benzyloxycarbonylamino-α-bromoacetophenone having a melting point of 141°–143° C. was obtained.

Reference example 11

In 100 ml. of toluene was dissolved 5 g. of 2,6-dichloro-4-acetylphenyl isocyanate and after adding 10 ml. of anhydrous 2-methoxy ethanol to the solution, the mixture was refluxed for 2 hours under heating. The reaction mixture was cooled, washed thrice each with 200 ml. of water, and dried over anhydrous magnesium sulfate. The mixture was then filtered and the filtrate obtained was concentrated under reduced pressure. Then, by recrystallizing the residue formed from a mixture of benzene and n-hexane, 5.85 g. of 3,5-dichloro-4-(2-methoxyethoxy)carbonylaminoacetophenone having a melting point of 90°–92° C. was obtained.

Furthermore, by following the similar procedure as in Reference example 2-c) using 5.85 g. of the product above obtained and 3.06 g. of bromine, 6.0 g. of 3,5-dichloro-4-(2-methoxyethoxy)carbonylamino-α-bromoacetophenone having a melting point of 98°–100° C. was obtained.

Reference example 12

(a) In 80 ml. of toluene was dissolved 4 g. of 2,6-dichloro-4-acetylphenyl isocyanate and anhydrous methylamine was passed through the solution at room temperature, whereby crystals were formed. The crystals were recovered by filtration and recrystallized from ethanol to provide 3.9 g. of 3,5-dichloro-4-methylcarbamoylaminoacetophenone having a melting point of 239°–241° C.

(b) In 50 ml. of acetic acid was dissolved 0.5 g. of 3,5-dichloro-4-methylcarbamoylaminoacetophenone at 60°–70° C. and after passing hydrogen bromide through the solution, 0.31 g. of bromine was added to the solution. Then, the solvent was distilled off from the reaction mixture under reduced pressure and the residue formed was recrystallized from ethanol to provide 0.4 g. of 3,5-dichloro-4-methylcarbamoylamino-α-bromoacetophenone having a melting point of 209°–211° C. (decomp.).

Reference example 13

In 150 ml. of toluene was dissolved 4 g. of 2,6-dichloro-4-acetylphenyl isocyanate and dry ammonia gas was passed through the solution at room temperature whereby crystals were formed. The crystals were recovered and recrystallized from ethanol to provide 4.12 g. of 4-carbamoylamino-3,5-dichloroacetophenone having a melting point of 207°–209° C.

Furthermore, 300 ml. of acetic acid was added to 4.6 g. of 4-carbamoylamino-3,5-dichloroacetophenone and the mixture was heated to 70°–80° C. Then, after passing hydrogen bromide through the solution obtained, 2.98 g. of bromine was added thereto. After the reaction was over, the solvent was distilled off from the reaction mixture under reduced pressure and the residue formed was recrystallized from ethanol to provide 2.4 g. of 4-carbamoylamino-3,5-dichloro-α-bromoacetophenone having a melting point of 201°–202° C. (decomp.).

Reference example 14

In 30 ml. of absolute methanol was suspended 1 g. of 4-carbamoylamino-3,5-dichloro-α-bromoacetophenone and the suspension was cooled with ice-water and after adding thereto 0.1 g. of sodium borohydride under cooling, the mixture was stirred for 30 minutes. After the reaction was over, 4.2 ml. of a 1.44 N hydrochloric acid-ethanol solution was added to the reaction mixture followed by stirring for 5 minutes and after adding an excessive amount of sodium carbonate to the mixture, the resultant mixture was further stirred for 15 minutes.

The solvent was distilled off from the reaction mixture under reduced pressure and the residue obtained was extracted with 50 ml. of ethyl acetate. The ethyl acetate extract was washed with a saturated aqueous sodium chloride solution and dried over anhydrous magnesium sulfate. The mixture was filtered and the solvent was distilled off from the mixture under reduced pressure to provide 0.86 g. of oily 4-carbamoylamino-3,5-dichloro-α-bromo-methyl benzyl alcohol.

Nuclear magnetic resoance spectra (D$_6$-DMSO): δ(p.p.m.): 3.62 (m, 2H, —CH$_2$Br), 4.80 (m, 1H, >CH—OH), 7.46 (s, 2H, H of benzene ring).

Reference example 15

(a) A mixture of 1 g. of 4-amino-3-bromo-4-chloroacetophenone, 1 g. of phosgene, and 10 ml. of toluene was heated to 150° C. for 12 hours in a sealed tube. After cooling the reaction mixture, 5 ml. of methanol was added thereto and the mixture was refluxed for one hour under heating. After the reaction was over, the reaction mixture obtained was cooled and concentrated under reduced pressure. Then, by recrystallizing the solid product thus obtained from a mixture of benzene and n-hexane, 0.8 g. of 3-bromo-5-chloro-4-methoxycarbonylaminoactophenone having a melting point of 135°-136° C. was obtained.

(b) A solution of 0.42 g. of bromine in 2 ml. of chloroform was gradually added dropwise to a solution of 0.8 g. of 3-bromo-5-chloro-4-methoxycarbonylaminoacetophenone in 10 ml. of chloroform with stirring at room temperature. After the reaction was over, the reaction mixture was concentrated under reduced pressure to provide a crystalline residue. The residue was then washed with a mixture of ether and n-hexane and dried to provide 0.8 g. of 3-bromo-5-chloro-4-methoxycarbonylamino-α-bromoacetophenone having a melting point of 146°-148° C.

Reference example 16

(a) After adding 2.0 g. of sodium carbonate to a solution of 3.8 g. of 4-methoxycarbonylaminoacetophenone in 20 ml. of chloroform, a chloroform solution containing 1.4 g. of chlorine was gradually added dropwise to the mixture with stirring. After the reaction was over, the reaction mixture was concentrated under reduced pressure and the solid product thus obtained was recrystallized from benzene to provide 2.5 g. of 3-chloro-4-methoxycarbonylaminoacetophenone having a melting point of 100°-101° C.

(b) A solution of 1.4 g. of bromine in 3 ml. of chloroform was gradually added dropwise to a solution of 1.9 g. of 3-chloro-4-methoxycarbonylaminoacetophenone in 20 ml. of chloroform. After the reaction was over, the reaction mixture was concentrated under reduced pressure to provide a solid product, which was recrystallized from a mixture of benzene and n-hexane to provide 2.3 g. of 3-chloro-4-methoxycarbonylamino-α-bromoacetophenone having a melting point of 150°-151° C.

Reference example 17

(a) A mixture of 5 g. of 4-amino-3,5-dichloroacetophenone, 5 ml. of phosgene, and 30 ml. of toluene was heated to 150° C. for 24 hours in a sealed tube. The reaction mixture was cooled and concentrated under reduced pressure to provide crude 4-acetyl-2,6-dichlorophenyl isocyanate. The crude product was dissolved in 100 ml. of toluene and then dry dimethylamine was passed through the solution for one hour at room temperature. The reaction mixture was concentrated under reduced pressure and the residue formed was recrystallized from a mixture of benzene and n-hexane to provide 2.58 g. of 3,5-dichloro-4-N,N-dimethylcarbamoylaminoacetophenone having a melting point of 138°-140° C.

(b) Hydrogen bromide was passed through a solution of 2.58 g. of 3,5-dichloro-4-N,N-dimethylcarbamoylaminoacetophenone in 50 ml of chloroform and 50 ml. of acetic acid and then 1.5 g. of bromine was further added thereto. After the reaction was over, the solvent was distilled off from the reaction mixture under reduced pressure. The residue formed was applied to a silica gel column chromatography and eluted with a mixture of chloroform and ethyl acetate as eluting solution. Then, by distilling off the solvents from the eluate under reduced pressure, 2.87 g. of 3,5-dichloro-4-N,N-dimethylcarbamoylamino-α-bromoacetophenone having a melting point of 122°-125° C. was obtained.

Reference example 18

(a) A mixture of 5 g. of 4-amino-3,5-dichloroacetophenone, 5 ml. of phosgene, and 30 ml. of toluene was heated to 150° C. for 24 hours in a sealed tube. The reaction mixture was cooled and concentrated under reduced pressure to provide crude 4-acetyl-2,6-dichlorophenyl isocyanate. The crude product was dissolved in 150 ml. of toluene and then 5 ml. of aniline was added to the solution. The crystals thus formed were recovered by filtration and recrystallized from ethanol to provide 4.56 g. of 3,5-dichloro-4-phenylcarbamoylaminoacetophenone having a melting point of 239°-240° C.

(b) In 200 ml. of acetic acid was dissolved 4.56 g. of 3,5-dichloro-4-phenylcarbamoylaminoacetophenone at 80° C. and then 2.26 g. of bromine was added to the solution. After the reaction was over, the solvent was distilled off from the reaction mixture under reduced pressure. Then, the residue formed was recrystallized from ethanol to provide 1.06 g. of 3,5-dichloro-4-phenylcarbamoylamino-α-bromoacetophenone having a melting point of 213°-215° C.

Reference example 19

(a) A mixture of 5 g. of 4-amino-3,5-dichloroacetophenone, 5 ml. of phosgene, and 30 ml. of toluene was heated to 150° C. for 24 hours at a sealed tube. The reaction mixture obtained was cooled and concentrated under a reduced pressure to provide crude 4-acetyl-2,6-dichlorophenyl isocyanate. The crude product was dissolved in 100 ml. of toluene and after adding 10 g. of cyclohexanol to the solution, the mixture was stirred overnight at 100° C. The reaction mixture was cooled and concentrated under reduced pressure. The residue formed was then recrystallized from a mixture of benzene and n-hexane to provide 4.3 g. of 3,5-dichloro-4-cyclohexyloxycarbonylaminoacetophenone having a melting point of 88°-89° C.

(b) In 30 ml. of chloroform was dissolved 4.3 g. of 3,5-dichloro-4-cyclohexyloxycarbonylaminoacetophenone and then a solution of 2.08 g. of bromine in 5 ml. of chloroform was added to the solution thus obtained with stirring at room temperature. The mixture was further stirred for 30 minutes and then concentrated under reduced pressure, whereby crystals were formed. The crystals were recrystallized from a mixture of benzene and n-hexane to provide 4.81 g. of 3,5-dichloro-4-cyclohexyloxycarbonylamino-α-bromoacetophenone having a melting point of 114°-116° C.

Reference example 20

By following the similar procedure as in Reference example 12-a) using 6 g. of 2,6-dichloro-4-acetylphenyl isocyanate and anhydrous ethylamine, 5.47 g. of 3,5- dichloro-4-ethylcarbamoylaminoacetophenone was obtained. Melting point 233°–235° C. (decomp.).

Furthermore, by following the similar procedure as in Reference example 12-b) using 5.47 g. of 3,5-dichloro-4-ethylcarbamoylaminoacetophenone and 3.18 g. of bromine, 5.71 g. of 3,5-dichloro-4-ethylcarbamoylamino-α-bromoacetophenone having a melting point of 202°–204° C. was obtained.

Now, the processes of producing the compounds of this invention using the starting materials prepared by the aforementioned reference examples will be explained by the following examples.

EXAMPLE 1

(a) In 20 ml. of chloroform was dissolved 2.1 g. of 3,5-dichloro-4-methylamino-α-bromoacetophenone and after adding 3 ml. of tert-butylamine to the solution, the mixture was refluxed for 2 hours under heating. The reaction mixture was concentrated under reduced pressure and after adding 10 ml. of 10% hydrochloric acid to the residue formed, the mixture was extracted thrice each with 10 ml. of ether. The aqueous layer formed was alkalinified with sodium carbonate, and extracted with benzene. The benzene extract was dried with magnesium sulfate. After filtering, 5 ml. of 2 N hydrochloric acid ethanol was added to the filtrate and then the solvent was distilled off from the mixture to provide a solid product, which was washed with a mixture of ethanol and ethyl acetate (1:5) to provide 0.7 g. of the white crystal of 3,5-dichloro-4-methylamino-α-tert-butylaminoacetophenone dihydrochloride. The melting point of the product was 209°–211° C.

(b) In 10 ml. of ethanol was dissolved 0.5 g. of 3,5-dichloro-4-methylamino-α-tert-butylaminoacetophenone dihydrochloride and after adding 0.2 g. of sodium borohydride to the solution, the mixture was stirred for one hour at room temperature. After adding water to the reaction mixture, the mixture was concentrated under reduced pressure and the residue formed was extracted with benzene. The extract was washed with water and dried over magnesium sulfate. Then, after filtering, the solvent was distilled off from the filtrate, whereby 0.35 g. of the white crystal of 3,5-dichloro-4-methylamino-α-(N-tert-butylaminomethyl) benzyl alcohol was obtained. The melting point of the product was 101°–102° C.

Nuclear magnetic resonance spectra (CDCl$_3$): δ: 1.08 (9H, s, —C(CH$_3$)$_3$), 2.96 (3H, s, >N—CH$_3$), 4.46 (1H, d of d,

7.21 (2H, s, H of benzene ring).

EXAMPLE 2

In 8 ml. of tert-butylamine was dissolved 0.4 g. of 3,5-dichloro-4-methoxycarbonylamino-α-bromomethylbenzyl alcohol and the solution was heated overnight to 50° C. in a sealed tube. After cooling, the reaction mixture was concentrated under reduced pressure to provide a yellow oily material. The oily material was dissolved in 50 ml. of methanol and after adding 5 ml. of water and excessive amount of sodium carbonate to the solution, the mixture was stirred for 30 minutes. The mixture was concentrated under reduced pressure and the residue was dissolved in 50 ml. of chloroform and washed with saturated aqueous sodium chloride solution. The mixture was dried over anhydrous magnesium sulfate and concentrated to provide a yellow oily material. The oily material was applied to a 15 ml. silica gel column chromatography and developed after passing 300 ml. of chloroform through the column, methanol was used as eluting solution) to provide 0.09 g. of 3,5-dichloro-4-methoxycarbonylamino-α-tert-butylaminomethylbenzyl alcohol having a melting point of 162°–164° C.

Nuclear magnetic resonance spectra (CDCl$_3$): δ: 1.80 (s, 9H, —C(CH$_3$)$_3$), 2.77 (m, 2H,

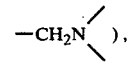

3.74 (s, 3H, —COOCH$_3$), 4.50 (m, 1H,

7.34 (s, 2H, H of benzene ring).

EXAMPLE 3

A mixture of 1 g. of 3,5-dichloro-4-methylamino-α-bromoacetophenone, 2g. of 1,1-dimethyl-2-phenylethylamine, 0.5 g. of anhydrous sodium carbonate, and 20 ml. of chloroform was stirred for 3 hours at room temperature. After filtering off insoluble materials, 10 ml. of ethanol and 0.2 g. of sodium borohydride was added to the chloroform solution obtained and the mixture was stirred for one hour at room temperature. The reaction mixture was concentrated under a reduced pressure and after adding 20 ml. of 5% acetic acid to the residue thus obtained, the mixture was extracted with ethyl acetate. The extract was washed with 10 ml. of 5% acetic acid solution and after adding 20 ml. of 5% hydrochloric acid, the mixture was vigorously shaked. The aqueous layer formed was separated, washed twice each with 10 ml. of ethyl acetate. The aqueous solution was basified with sodium carbonate, and extracted with benzene. The benzene extract was washed with water and dried over anhydrous magnesium sulfate. After filtering, the filtrate was concentrated under reduced pressure to provide 0.7 g. of an oily material. The oily material was dissolved in 2 ml. of ethanol and then 120 mg. of fumaric acid was added to the solution. The resultant solution was concentrated under reduced pressure and the residue obtained was dissolved in ethyl acetate. By allowing to stand the solution, 0.4 g. of 3,5-dichloro-4-methylamino-α-(α,α-dimethylphenetylaminomethyl)benzyl alcohol ½ fumarate having a melting point of 150°–152° C. was obtained.

Nuclear magnetic resonance spectra (D$_6$-DMSO): δ: 1.09 (6H, s, —C(CH$_3$)$_2$), 2.92 (3H, s, >N—CH$_3$), 4.74 (1H, m, >CHOH).

EXAMPLE 4

By following the similar procedure as in Example 3 using 1 g. of 3,5-dichloro-4-methylamino-α-bromoacetophenone, 2.5 g. of 1-methyl-2-p-methoxyphenylethylamine, and 0.5 g. of anhydrous sodium carbonate, 0.4 g. of the white crystal of 3,5-dichloro-4-methylamino-α-(α-methyl-p-methoxyphenetylaminomethyl)benzyl alcohol ½ fumarate having a melting point of 89° C. was obtained.

Nuclear magnetic resonance spectra (D₆-DMSO): δ: 2.92 (3H, s, >N—CH₃), 3.70 (3H, s, —O—CH₃), 4.75 (1H, m, >CHOH), 6.52 (1H, s,

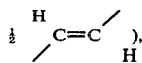

7.32 (2H, s, H of benzene ring), 6.82, 7.12 (4H, AB-quartet, H of the benzene ring of

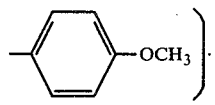

EXAMPLE 5

By following the similar procedure as in Example 3 using 1 g. of 3,5-dichloro-4-methylamino-α-bromoacetophenone, 2 g. of 1-methyl-2-p-hydroxyphenylethylamine, and 0.5 of anhydrous sodium carbonate, 0.25 g. of the white crystal of 3,5-dichloro-4-methylamino-α-(α-methyl-p-hydroxyphenetylaminomethyl)benzyl alcohol ½ fumarate was obtained.

Nuclear magnetic resonance spectra (D₆-DMSO): δ: 0.99 (3H, d, >CH—CH₃), 2.91 (3H, s, >N—CH₃), 4.74 (1H, m, >CH—CH), 7.31 (2H, s, H of benzene ring), 6.68, 6.97 (4H, AB-quartet, H of the benzene ring of

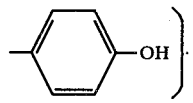

EXAMPLE 6

A mixture of 1 g. of 3,5-dichloro-4-ethylamino-α-bromoacetophenone, 2 ml. of tert-butylamine, and 20 ml. of chloroform was stirred for one hour at 30°–40° C. After the reaction was over, 0.2 g. of sodium borohydride and 20 ml. of ethanol were added to the reaction mixture. The mixture was then stirred for 2 hours at room temperature and concentrated under reduced pressure. The residue formed was added to 20 ml. of 5% aqueous hydrochloric acid solution and washed with ethyl acetate. The aqueous layer formed was basified with sodium carbonate and extracted with ethyl acetate. The ethyl acetate extract was dried over anhydrous magnesium sulfate and concentrated under reduced pressure to provide 0.55 g. of an oily material. After dissolving 0.45 g. of the oily material in 1.5 ml. of 1 N hydrochloric acid-ethanol ether was further added to the solution, whereby crystals were formed. The crystals were recovered by filtration to provide 0.43 g. of the white crystal of 3,5-dichloro-4-ethylamino-α-(tert-butylaminomethyl)benzyl alcohol mono-hydrochloride having a melting point of 215° C.

Nuclear magnetic resonance spectra (D₆-DMSO): δ: 1.08 (3H, t, —CH₂—CH₃), 1.35 (9H, s, —C(CH₃)₃), 3.04 (2H, m, —CH(OH)—CH₂—), 3.34 (2H, q, —CH₂—CH₃), 5.01 (1H, m, —CH(OH)—), 7.45 (2H, s, H of benzene ring).

EXAMPLE 7

A mixture of 1.3 g. of 3,5-dibromo-4-methylamino-α-bromoacetophenone, 2 ml. of tert-butylamine, and 20 ml. of chloroform was stirred for 4 hours at room temperature and then the reaction mixture was treated by the similar procedure as in Example 6 to provide 1.0 g. of the white crystal of 3,5-dibromo-4-methylamino-α-(tert-butylaminomethyl)benzylalcohol having a melting point of 85° C.

Nuclear magnetic resonance spectra (CDCl₃): δ: 1.07 (9H, s, —C(CH₃)₃), 2.50, 2.74 (2H, d of AB-q, —CH(OH)—CH₂—), 2.90 (3H, s, >N—CH₃), 4.47 (1H, d of d, >CH(OH)), 7.45 (2H, s, H of benzene ring).

EXAMPLE 8

A mixture of 1 g. of 3,5-dibromo-4-methoxycarbonylamino-α-bromoacetophenone, 1 ml. of tert-butylamine, and 20 ml. of a mixture of chloroform and acetonitrile (volume ratio 1:1) was stirred for one hour at room temperature and the reaction mixture was treated by the similar procedure as in Example 6 to provide 0.3 g. of the white crystal of 3,5-dibromo-4-methoxycarbonylamino-α-(tert-butylaminomethyl)benzyl alcohol having a melting point of 150°–152° C.

Nuclear magnetic resonance spectra (CDCl₃): δ: 1.09 (9H, s, —C(CH₃)₃), 2.52, 2.88 (2H, d of AB-q, —CH(OH)—CH₂—), 3.77 (3H, s, —OCH₃), 4.54 (1H, d of d, —CHOH—), 7.56 (2H, s, H of benzene ring).

EXAMPLE 9

A mixture of 1.25 g. of 3,5-dichloro-4-methoxycarbonylamino-α-bromoacetophenone, 0.8 g. of tert-butylamine, and 20 ml. of chloroform was stirred for 3 hours at 30°–40° C. After the reaction was over, the reaction mixture obtained was washed with 50 ml. of water and dried over anhydrous magnesium sulfate and then the filtrate was concentrated under reduced pressure. The residue formed was dissolved in 20 ml. of ethanol and after adding 0.15 g. of sodium borohydride to the solution, the mixture was stirred for one hour at room temperature and then concentrated under reduced pressure. The residue formed was added to a mixture of 10 ml. of a 2 N aqueous hydrochloric acid solution and 30 ml. of water and after stirring for one hour, insoluble materials were filtered off. Then, the filtrate was basified with an excessive amount of sodium carbonate and after saturating the alkalinified filtrate with sodium chloride, the mixture was extracted thrice each with 30 ml. of ethyl acetate. The ethyl acetate layer thus extracted was washed thrice each with 100 ml. of a saturated aqueous sodium chloride solution and dried over anhydrous magnesium sulfate. After filtering, the filtrate was concentrated under reduced pressure and the residue formed was recrystallized from ethyl acetate to provide 0.35 g. of 3,5-dichloro-4-methoxycarbonylamino-α-(tert-butylaminomethyl)benzyl alcohol having a melting point of 162°–164° C.

| Elemental analysis for C₁₄H₂₀N₂O₃Cl₂: | | | |
|---|---|---|---|
| | C | H | N |
| Calculated: | 50.16% | 6.01% | 8.36% |
| Found: | 49.99% | 5.94% | 8.20%. |

EXAMPLE 10

A mixture of 2.5 g. of 3,5-dichloro-4-ethoxycarbonylamino-α-bromoacetophenone, 2 ml. of tert-butylamine, and 30 ml. of chloroform was stirred for 3 hours at 30° C. and then the reaction mixture was treated with the similar procedure as in Example 9 to provide 0.2 g. of 3,5-dichloro-4-ethoxycarbonylamino-α-(tert-butylaminomethyl)benzyl alcohol having a melting point of 176°–178° C.

Elemental analysis for $C_{15}H_{22}N_2O_3Cl_2$:

|  | C | H | N |
|---|---|---|---|
| Calculated: | 51.59% | 6.35% | 8.02% |
| Found: | 51.62% | 6.31% | 8.11% |

In 10 ml. of methanol was dissolved 0.92 g. of 3,5-dichloro-4-ethoxycarbonylamino-α-(tert-butylaminomethyl)benzyl alcohol and then 2 ml. of 1.44 N hydrochloric acid-ethanol was added to the solution. The solvent was distilled off from the reaction mixture under reduced pressure and ethyl acetate was added to the residue formed, whereby crystals were formed. The crystals were recovered by filtration, washed with ethyl acetate and dried to provide 0.85 g. of 3,5-dichloro-4-ethoxycarbonylamino-α-(tert-butylaminomethyl)benzyl alcohol hydrochloride having a melting point of 230°–232° C. (decomp.).

EXAMPLE 11

A mixture of 2 g. of 3,5-dichloro-4-n-propoxycarbonylamino-α-bromoacetophenone, 0.87 g. of tert-butylamine, and 50 ml. of chloroform was stirred for 3 hours at 30° C. and then the reaction mixture was treated with the similar procedure as in Example 9 to provide 0.16 g. of 3,5-dichloro-4-n-propoxycarbonylamino-α-(tert-butylaminomethyl)benzyl alcohol having a melting point of 156°–158° C.

Elemental analysis for $C_{16}H_{24}N_2O_3Cl_2$:

|  | C | H | N |
|---|---|---|---|
| Calculated: | 52.90% | 6.66% | 7.71% |
| Found: | 52.98% | 6.75% | 7.54% |

EXAMPLE 12

A mixture of 2 g. of 3,5-dichloro-4-isopropoxycarbonylamino-α-bromoacetophenone, 0.87 g. of tert-butylamine, and 50 ml. of chloroform was stirred for 3 hours at 30°–35° C. and then the reaction mixture was treated by the similar procedure as in Example 9 to provide 0.47 g. of 3,5-dichloro-4-isopropoxycarbonylamino-α-(tert-butylaminomethyl)benzyl alcohol having a melting point of 173°–175° C.

Elemental analysis for $C_{16}H_{24}N_2O_3Cl_2$:

|  | C | H | N |
|---|---|---|---|
| Calculated: | 52.90% | 6.66% | 7.71% |
| Found: | 52.82% | 8.74% | 7.46 |

EXAMPLE 13

A mixture of 3 g. of 3,5-dichloro-4-benzyloxycarbonylamino-α-bromoacetophenone, 1.15 g. of tert-butylamine, and 50 ml. of chloroform was stirred overnight at room temperature and then the reaction mixture was treated by the similar procedure as in Example 9 to provide 3,5-dichloro-4-benzyloxycarbonylamino-α-(tert-butylaminomethyl)benzyl alcohol. By treating the product with a 1.44 N hydrochloric acid-ethanol solution, 0.13 g. of the crystal of 3,5-dichloro-4-benzyloxycarbonylamino-α-(tert-butylaminomethyl)benzyl alcohol hydrochloride having a melting point of 209°–212° C. was obtained.

Nuclear magnetic resonance spectra (D$_6$-DMSO):δ(p.p.m.): 1.30 (s, 9H, —C(CH$_3$)$_3$), 3.04 (m, 2H, —CH$_2$N<), 5.14 (s, 2H,

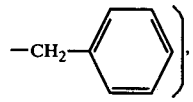), 7.38 (s, 5H,

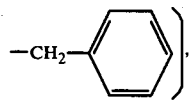), 7.60 (s, 2H, H of benzene ring).

EXAMPLE 14

A mixture of 2.5 g. of 3,5-dichloro-4-(2-methoxyethoxy)carbonylamino-α-bromoacetophenone, 1.05 g. of tert-butylamine, and 50 ml. of chloroform was stirred for one hour at 35° C. and then the reaction mixture was treated by the similar procedure as in Example 13 to provide 0.8 g. of 3,5-dichloro-4-(2-methoxyethoxy)carbonylamino-α-(tert-butylaminomethyl)benzyl alcohol hydrochloride, which was recrystallized from a mixture of ethanol and ether.

Melting point: 211°–214° C.

Elemental analysis for $C_{18}H_{25}N_2O_4Cl_3$:

|  | C | H | N |
|---|---|---|---|
| Calculated: | 46.22% | 6.06% | 6.74% |
| Found: | 46.01% | 6.28% | 6.62% |

EXAMPLE 15

In a mixture of 20 ml. of anhydrous dimethylformamide and 20 ml. of ethyl acetate was dissolved 0.5 g. of 3,5-dichloro-4-methylcarbamoylamino-α-bromoacetophenone and after cooling the solution to a temperature of from −20° C. to −30° C., a solution of 0.24 g. of tert-butylamine in 5 ml. of ethyl acetate was added dropwise to the solution followed by stirring for 30 hours at −20° C.

After the reaction was over, 40 ml. of absolute ethanol was added to the reaction mixture at −30° C. and then 0.2 g. of sodium borohydride was added to the mixture followed by stirring for 4 days at −20° C.

After the reaction was over, the temperature of the reaction mixture was raised to room temperature and then the solvent was distilled off from the reaction mixture at a temperature lower than 50° C. under reduced pressure. To the residue formed were added 100 ml. of water and 10 ml. of 2 N hydrochloric acid followed by stirring for one hour and then insoluble materials were filtered off. The filtrate was basified with sodium carbonate and after saturating the basified filtrate with sodium chloride, the mixture was extracted with 50 ml. of ethyl acetate.

The ethyl acetate extract thus obtained was washed with a saturated aqueous sodium chloride solution and dried over anhydrous magnesium sulfate. Then, after filtering, the filtrate was concentrated under reduced pressure and the residue formed was recrystallized from ethyl acetate to provide 0.13 g. of 3,5-dichloro-4-methylcarbamoylamino-α-(tert-butylaminomethyl)benzyl alcohol having a melting point of 93°–97° C.

Nuclear magnetic resonance spectra (CDCl$_3$, D$_6$-DMSO): δ(p.p.m.): 1.08 (s, 9H, —C(CH$_3$)$_3$), 2.72 (d, 3H, —CH$_3$), 4.54 (m. 1H, >CHOH), 7.36 (s, 2H, H of benzene ring).

EXAMPLE 16

In a mixture of 50 ml. of anhydrous dimethylformamide and 50 ml. of ethyl acetate was dissolved 1.3 g. of 3,5-dichloro-4-carbamoylamino-α-bromoacetophenone and after cooling the solution to a temperature of from −20° C. to −30° C., a solution of 0.7 g. of tertbutylamine in 5 ml. of ethyl acetate was added dropwise to the solution followed by stirring for 20 hours at −20° C.

After the reaction was over, 80 ml. of absolute ethanol was added to the reaction mixture at a temperature of from −20° C. to −30° C. and then 0.4 g. of sodium borohydride was added to the mixture followed by stirring for 2 days at −20° C. to −30° C.

After the reaction was over, the temperature of the reaction mixture formed was raised to room temperature and then the solvent was distilled off from the reaction mixture at a temperature lower than 50° C. under reduced pressure. To the residue formed were added 100 ml. of water and 10 ml. of 2 N hydrochloric acid and after stirring the mixture for one hour, insoluble materials were filtered off from the mixture. The filtrate was basified with sodium carbonate and after saturating the basified filtrate with sodium chloride, the mixture was extracted with 50 ml. of ethyl acetate. The ethyl acetate extract obtained was washed with a saturated aqueous sodium chloride solution, dried over anhydrous magnesium sulfate and then concentrated under reduced pressure. By subjecting the residue formed to a column chromatography, 0.02 g. of the oily material of 3,5-dichloro-4-carbamoylamino-α-(tert-butylaminomethylObenzyl alcohol was obtained.

Nuclear magnetic resonance spectra (D$_6$-acetone): δ(p.p.m.): 1.25 (s, 9H, —C(CH$_3$)$_3$), 2.96 (m, 2H, >CH$_2$N<), 4.82 (m, 1H, >CH—OH), 7.45 (n, 2H, H of benzene ring).

EXAMPLE 17

A mixture of 0.86 g. of 3,5-dichloro-4-carbamoylamino-αbromomethylbenzyl alcohol and 10 ml. of tert-butylamine was heated to 90°–100° C. for 2 days in a sealed tube. After cooling the reaction mixture, the solvent was distilled off under reduced pressure and after adding to the residue formed 50 ml. of ethyl acetate, 50 ml. of water, and an excessive amount of sodium carbonate followed by stirring for 30 minutes, sodium chloride was added to the mixture until the mixture was saturated. Then, the mixture was separated into an ethyl acetate layer and an aqueous layer. The ethyl acetate layer formed was washed with a saturated aqueous sodium chloride solution, and then dried over anhydrous magnesium sulfate. Then, after filtering, the solvent was distilled off from the filtrate under reduced pressure. By recrystallizing the residue from ethyl acetate, 0.24 g. of 3,5-dichloro-4-tert-butylcarbamoylamino-α-(tert-butylaminomethyl)benzyl alcohol having a melting point of 167°–169° C. was obtained.

Elemental analysis for C$_{17}$H$_{27}$N$_3$O$_2$Cl$_2$:

|  | C | H | N |
|---|---|---|---|
| Calculated: | 54.26% | 7.23% | 11.17% |
| Found: | 54.24% | 7.31% | 10.97% |

EXAMPLE 18

A mixture of 0.7 g. of 3-bromo-5-chloro-4-methoxycarbonylamino-α-bromoacetophenone, 0.7 ml. of tert-butylamine, and 10 ml. of acetonitrile was stirred for 30 minutes at 5°–15° C. After the reaction was over, 0.2 g. of sodium borohydride and 20 ml. of ethanol was added to the reaction mixture and then the mixture was stirred for 2 hours at room temperature. Thereafter, the mixture was concentrated under reduced pressure.

To the residue obtained was added 20 ml. of a 5% aqueous hydrochloric acid solution and then the mixture was washed twice each with ethyl acetate. The aqueous solution thus obtained was alkalinified with sodium carbonate, and extracted with ethyl acetate. Then, the ethyl acetate extract was dried over anhydrous magnesium sulfate and concentrated under reduced pressure to provide 0.32 g. of 3-bromo-5-chloro-4-methoxycarbonylamino-α-(tert-butylaminomethyl)-benzyl alcohol.

By adding 10 ml. of ethanol to a mixture of 0.19 g. of the product thus obtained and 0.03 g. of fumaric acid, 0.18 g. of 3-bromo-5-chloro-4-methoxycarbonylamino-α-(tert-butylaminomethyl)benzyl alcohol ½ fumarate was precipitated.

Melting point: 236°–238° C. (decomp.).

EXAMPLE 19

A mixture of 1.0 g. of 3,5-dichloro-4-ethoxycarbonylamino-α-bromoacetophenone, 1.0 g. of 1-methyl-2-p-methoxyphenylethylamine. 0.5 g. of sodium carbonate and 50 ml. of chloroform was stirred for 3 hours at room temperature. After filtering off insoluble materials from the reaction mixture, 10 ml. of ethanol and 0.4 g. of sodium borohydride were added to the filtrate and after stirring overnight the mixture, the solvent was distilled off from the mixture under reduced pressure. The residue was extracted with 100 ml. of ethyl acetate and the extract was washed with water and dried over anhydrous magnesium sulfate and then concentrated under reduced pressure. The residue was purified by a silica gel column chromatography and the oily product obtained was dissolved in 30 ml. of methanol. Then, 0.056 mg. of fumaric acid was added to the solution and the mixture was concentrated under reduced pressure. By reprecipitating the residue from chloroform- n-hexane, 0.3 g. of 3,5-dichloro-4-ethoxycarbonylamino-α-(1-methyl-2-p-methoxyphenylethylaminomethyl)benzyl alcohol ½ fumarate was obtained.

Nuclear magnetic resonance spectra (D$_6$-DMSO):

δ(p.p.m.):

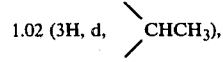

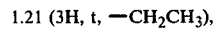

2.96 (3H, m, N—CH—CH₂ and N—CHCH₂—),
     |            |
     CH₃

3.73 (3H, s, —⟨C₆H₄⟩—OCH₃ ), 4.10 (2H, q, —CH₂CH₃), 4.80 (1H, m, \CH—OH), 6.57 (1H, s, ½ —CH),
            ‖
            HC—

7.02 (4H, AB-q, —⟨C₆H₄⟩—OCH₃ ), 7.54 (2H, s,

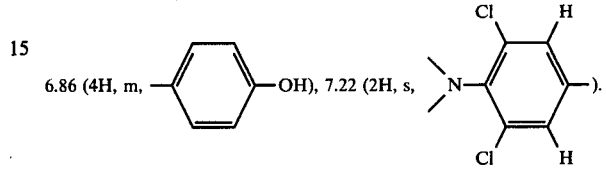

).

EXAMPLE 20

A mixture of 2.0 g. of 3,5-dichloro-4-ethoxycarbonylamino-α-bromoacetophenone, 0.75 g. of isopropylamine, and 20 ml. of chloroform was stirred for 3 hours at room temperature and then the reaction mixture was treated by the similar procedure as in Example 19 to provide 0.28 g. of 3,5-dichloro-4-ethoxycarbonylamino-α-isopropylaminomethylbenzyl alcohol·½ fumarate having a melting point of 205°–206° C. (decomp.).

Elemental analysis for C₁₆H₂₂N₂O₅Cl₂:

|  | C | H | N |
|---|---|---|---|
| Calculated: | 48.87% | 5.64% | 7.12% |
| Found: | 48.94% | 5.74% | 7.34% |

EXAMPLE 21

In a mixture of 40 ml. of anhydrous dimethylformamide and 20 ml. of ethyl acetate was dissolved 1 g. of 3,5-dichloro-4-ethylcarbamoylamino-α-bromoacetophenone and after cooling the solution to a temperature of from −20° C. to −30° C., a solution of 0.45 g. of tert-butylamine in 5 ml. of ethyl acetate was added dropwise to the solution followed by stirring for 3 hours at −20° C. Then, the reaction mixture obtained was treated by the similar procedure as in Example 15 to provide 0.33 g. of 3,5-dichloro-4-ethylcarbamoylamino-α-tert-butylaminomethylbenzyl alcohol. The product was further recrystallized from ethyl acetate. Melting point 174° C.

Elemental analysis for C₁₅H₂₃N₃O₂Cl₂:

|  | C | H | N |
|---|---|---|---|
| Calculated: | 51.73% | 6.66% | 12.07% |
| Found: | 51.55% | 6.70% | 11.79% |

EXAMPLE 22

After stirring overnight a mixture of 1.6 g. of 3,5-dichloro-4-ethoxycarbonylamino-α-bromoacetophenone, 2.0 g. of 1-methyl-2-p-hydroxyphenylethylamine, 1 g. of sodium carobnate and 200 ml. of chloroform at room temperature, the reaction mixture obtained was treated by the similar procedure as in Example 19 to provide 0.5 g. of 3,5-dichloro-4-ethoxycarbonylamino-α-(1-methyl-2-p-hydroxyphenylethylaminomethyl)benzyl alcohol.

Nuclear magnetic resonance spectra (D₆-DMSO): δ(p.p.m.): 1.07 (2H, d, >CHCH₃), 1.28 (3H, t, —CH₂CH₃), 4.22 (2H, q, —CH₂CH₃), 4.54 (1H, m, >CHOH), 6.86 (4H, m, —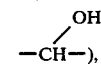—OH), 7.22 (2H, s,

).

EXAMPLE 23

A mixture of 2.0 g. of 3-chloro-4-methoxycarbonylamino-α-bromoacetophenone and 2.0 ml. of tert-butylamine was stirred in a mixture of 20 ml. of chloroform and 20 ml. of acetonitrile for one hour at room temperature. After the reaction was over, to the reaction mixture was added 20 ml. of ethanol and 0.5 g. of sodium borohydride and then the mixture was further stirred overnight at room temperature.

After the reaction was over, the reaction mixture was treated with the similar procedure as in Example 18 to provide 0.9 g. of the crystal of 3-chloro-4-methoxycarbonylamino-α-(N-tert-butylaminomethyl)benzyl alcohol having a melting point of 102° C.

Nuclear magnetic resonance spectra (CDCl₃): δ: 1.07 (9H, s, —C(CH₃)₃), 2.58, 2.88 (2H, d of AB-q, —CH₂N<), 3.79 (3H, s, —O—CH₃), 4.55 (1H, d of d,

OH
     /
—CH—), 7.27 (1H, d of d, H of the 2-position of benzene ring), 7.43 (1H, d, H of the 6-position of benzene ring), 7.13 (1H, d, H of the 5-position of benzene ring).

EXAMPLE 24

In a mixture of 40 ml. of anhydrous dimethylformamide and 20 ml. of ethyl acetate was dissolved 1.07 g. of 3,5-dichloro-4-phenylcarbamoylamino-α-bromoacetophenone and after adding dropwise to the solution a solution of 0.59 g. of tert-butylamine in 5 ml. of ethyl acetate at −20° to −30° C., the mixture was further stirred for 8 hours at −20° C. Then, after adding 40 ml. of absolute ethanol to the reaction mixture thus obtained at −30° C., 0.2 g. of sodium borohydride was added to the mixture and stirred for 4 days at −20° C.

After the reaction was over, the temperature of the reaction mixture was raised to room temperature and the solvent was distilled off from the reaction mixture at a temperature below 50° C. under reduced pressure. To the residue obtained were added 100 ml. of water and 10 ml. of 2 N hydrochloric acid and after stirring the mixture for one hour, insoluble materials were filtered off. The filtrate was basified with sodium carbonate and after saturating the basified filtrate with sodium chloride the mixture was extracted with 50 ml. of ethyl acetate. The ethyl acetate extract thus obtained was washed with a saturated aqueous sodium chloride solution and dried over anhydrous magnesium sulfate. After filtering, the solvent was distilled off from the filtrate under reduced pressure and the residue formed was recrystallized from ethyl acetate to provide 0.26 g. of 3,5-dichloro-4-phenylcarbamoylamino-α-(tert-butylaminomethyl)benzyl alcohol·½ hydrate. The product was recrystallized from a mixture of ethyl acetate and n-hexane. Melting point 171°–173° C. (decomp.).

Elemental analysis for $C_{19}H_{23}N_3O_2Cl_2 \cdot (H_2O)$

|  | C | H | N |
|---|---|---|---|
| Calculated: | 56.30% | 5.97% | 10.37% |
| Found: | 56.12% | 5.64% | 10.27% |

EXAMPLE 25

A mixture of 1 g. of 3,5-dichloro-4-N,N-dimethylcarbamoylamino-α-bromoacetophenone, 0.45 g. of tert-butylamine, and 50 ml. of chloroform was stirred overnight at room temperature. To the reaction mixture were added 20 ml. of ethanol and then 0.2 g. of sodium borohydride and after stirring the mixture for 2 hours at room temperature, the mixture was concentrated under reduced pressure. To the residue formed was added 20 ml. of a 5% aqueous hydrochloric acid solution, the mixture was washed with ethyl acetate. The aqueous solution thus obtained was basified with sodium carbonate and extracted with ethyl acetate. The ethyl acetate extract thus obtained was dried over anhydrous magnesium sulfate and concentrated under reduced pressure to provide 0.28 g. of 3,5-dichloro-4-N,N-dimethylcarbamoylamino-α-(tert-butylaminomethyl)benzyl alcohol. The product was dissolved in 20 ml. of methanol and after adding 0.05 g. of fumaric acid to the solution, the solvent was distilled off from the mixture under reduced pressure. The residue formed was dissolved in 4 ml. of 80% isopropyl alcohol and was allowed to stand overnight to provide 0.16 g. of 3,5-dichloro4-N,N-dimethylcarbamoylamino-α-(tert-butylaminomethyl)benzyl alcohol·½ fumarate having a melting point of 217°–221° C.

Nuclear magnetic resonance spectra ($D_6$-DMSO):
δ(p.p.m.): 1.21 (s, 9H, —C(CH$_3$)$_3$), 2.92 (s, 6H,

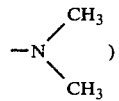
), 4.82 (m, 1H, >CH(OH)), 6.45 (s, 1H,

).

7.51 (s, 2H, H of benzene ring).

EXAMPLE 26

A mixture of 2 g. of 3,5-dichloro-4-cyclohexyloxycarbonylamino-α-bromoacetophenone, 0.8 g. of tert-butylamine, and 30 ml. of tetrahydrofuran was stirred for 2 hours at room temperature and then the reaction mixture was treated by the similar procedure as in Example 25 to provide 0.05 g. of 3,5-dichloro-4-cyclohexyloxycarbonylamino-α-(tertbutylaminomethyl)benzyl alcohol·½ fumarate having a melting point of 196°–198° C.

Elemental analysis for $C_{21}H_{30}N_2O_5Cl_2$:

|  | C | H | N |
|---|---|---|---|
| Calculated: | 54.67% | 6.55% | 6.07% |
| Found: | 54.40% | 6.94% | 6.40 |

EXAMPLE 27

In 50 ml. of chloroform was dissolved 3 g. of 3,5-dichloro4-ethoxycarbonylamino-α-bromoacetophenone. After adding 1.75 g. of cyclohexylamine to the solution, the mixture was stirred for 2.5 hours at room temperature. Then, 50 ml. of ethanol was added to the reaction mixture, and after cooling the mixture with ice-water, ,b 1 g. of sodium borohydride was added to the mixture, and the mixture was stirred for 2 hours at room temperature. After the reaction was over, the solvent was distilled off from the reaction mixture under reduced pressure, and 30 ml. of 5% hydrochloric acid aqueous solution was added to the residue thus obtained, and the mixture was washed with ethyl acetate. The aqueous solution thus obtained was alkalified with sodium carbonate, and the solution was extracted thrice with 50 ml. of ethyl acetate. The extract was dried over anhydrous magnesium sulfate and concentrated under reduced pressure. The crystals thus formed were washed with ether and recrystalized from ethyl acetate to provide 0.32 g. of 3,5-dichloro-4-ethoxycarbonylamino-α-(cyclohexylaminomethyl)benzyl alcohol having a melting point of 132°–134° C.

Nuclear magnetic resonance spectra (CDCl$_3$)

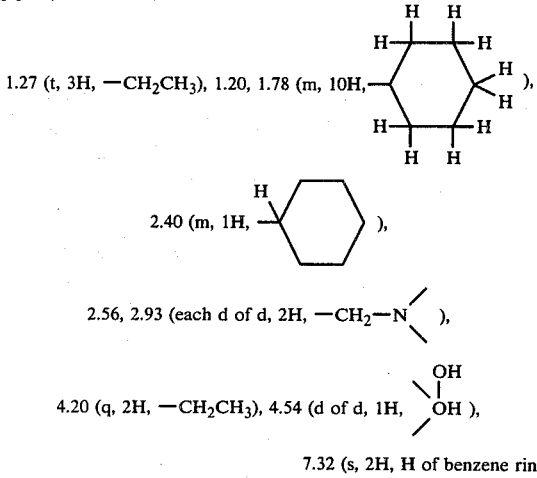

7.32 (s, 2H, H of benzene ring)

The following example illustrates the preparation of tablets using the compound of this invention:

| Formula: |  |
|---|---|
| 3,5-dichloro-4-ethoxycarbonylamino-α-(tert-butylaminomethyl)benzyl alcohol hydrochloride | 0.005 mg. |
| Lactose | 69.905 mg. |
| Starch | 27 mg. |
| Talc | 2.5 mg. |
| Magnesium stearate | 0.5 mg. |

The active substance was dissolved in a proper solvent and after adding lactose to the solution, the mixture was dried to provide a powder having uniform particle size. Starch was added to the powder and the mixture was granulated by means of a starch past and dried. To the dry granules were added talc and magnesium stearate and the mixture was formed a into tablet each having a diameter of about 7.0 mm. and a weight of about 100 mg.

What is claimed is:

1. A 4-substituted amino-α-aminomethylbenzyl alcohol derivative represented by the formula:

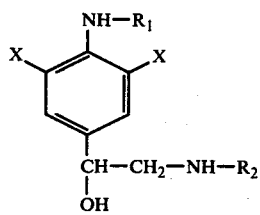

wherein X represents a halogen atom; $R_1$ represents a carbamoyl group, a mono- or dilower alkyl substituted carbamoyl group or a phenyl substituted carbamoyl group; and $R_2$ represents a lower alkyl group, a cycloalkyl group, or a group shown by the

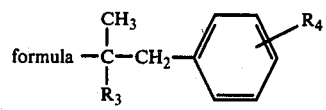

wherein $R_3$ represents a hydrogen atom or a lower alkyl group and $R_4$ represents a hydrogen atom, a hydroxy group or a lower alkoxy group and the pharmaceutically acceptable nontoxic salts thereof.

2. A 4-substituted amino-α-aminomethylbenzyl alcohol according to claim 1 which is 3,5-Dichloro-4-methylcarbamoylamino-α-(tert-butylaminomethyl)-benzyl alcohol and the pharmaceutically acceptable non-toxic salts thereof.

3. The 4-substituted amino-α-aminomethylbenzyl alcohol derivative as claimed in claim 1 wherein $R_2$ is a tert-butyl group.

* * * * *